(12) United States Patent
Hanlon et al.

(10) Patent No.: US 11,529,185 B2
(45) Date of Patent: *Dec. 20, 2022

(54) DUAL IRRIGATING BIPOLAR FORCEPS

(71) Applicant: Stryker Corporation, Kalamazoo, MI (US)

(72) Inventors: Matthew A. Hanlon, O'Fallon, MO (US); Matthew P. LaConte, Maryland Heights, MO (US)

(73) Assignee: Stryker Corporation, Kalamazoo, MI (US)

( * ) Notice: Subject to any disclaimer, the term of this patent is extended or adjusted under 35 U.S.C. 154(b) by 1373 days.

This patent is subject to a terminal disclaimer.

(21) Appl. No.: 15/875,576

(22) Filed: Jan. 19, 2018

(65) Prior Publication Data

US 2018/0140353 A1 May 24, 2018

Related U.S. Application Data

(63) Continuation of application No. 13/737,686, filed on Jan. 9, 2013, now Pat. No. 9,907,604.

(51) Int. Cl.
*A61B 18/14* (2006.01)
(52) U.S. Cl.
CPC .. *A61B 18/1442* (2013.01); *A61B 2018/1462* (2013.01); *A61B 2218/002* (2013.01)
(58) Field of Classification Search
CPC .................. A61B 2018/1462; A61B 2218/002
See application file for complete search history.

(56) References Cited

U.S. PATENT DOCUMENTS

| | | | |
|---|---|---|---|
| 4,041,952 A | 8/1977 | Morrison, Jr. et al. |
| 4,096,864 A | 6/1978 | Kletschka et al. |
| 4,938,761 A | 7/1990 | Ensslin |
| 5,217,460 A | 6/1993 | Knoepfler |
| 5,746,739 A | 5/1998 | Sutter |
| 6,096,037 A | 8/2000 | Mulier et al. |
| 6,210,411 B1 | 4/2001 | Hofmann et al. |
| 6,298,550 B1 | 10/2001 | Kirwan, Jr. |
| 6,863,669 B2 | 3/2005 | Spitzer |
| 7,621,911 B2 | 11/2009 | Ariola, Jr. |
| 9,907,604 B2 | 3/2018 | Hanlon et al. |
| 2002/0111579 A1 | 8/2002 | Moutafis et al. |
| 2003/0181909 A1 | 9/2003 | Kirwan |
| 2008/0200914 A1 | 8/2008 | Hanlon et al. |

OTHER PUBLICATIONS

510(k) Summary of Safety and Effectiveness K110924.

*Primary Examiner* — Jaymi E Della
(74) *Attorney, Agent, or Firm* — Howard & Howard Attorneys PLLC

(57) ABSTRACT

Bipolar electrosurgical forceps are provided with dual irrigating tubes that deliver irrigating liquid to the opposed surfaces of the tips of the forceps to prevent the sticking of body tissue to the tips. To reduce the manufacturing costs of the forceps and enable the forceps to be single use, disposable forceps, each tube of the dual irrigating tools is a plastic tube adhered along one of the opposing surfaces of the pair of forceps arms. Each tube also has a flat nozzle at the distal end of the tube that disburses irrigating liquid across the opposed surfaces of the forceps arm distal and tips.

20 Claims, 3 Drawing Sheets

DUAL IRRIGATING BIPOLAR FORCEPS

CROSS-REFERENCE TO RELATED APPLICATIONS

The present application is a continuation of U.S. patent application Ser. No. 13/737,686, filed Jan. 9, 2013, now issued as U.S. Pat. No. 9,907,604 and entitled "Dual Irrigating Bipolar Forceps," which is hereby incorporated by reference herein in its entirety.

DESCRIPTION OF THE RELATED ART

Bipolar electrosurgical forceps are typically constricted with a pair of electrode arms having proximal ends that are adapted to have electrical conductors removably attached to the proximal ends, and opposite distal ends with tips that contact and grasp or pinch body tissue between the tips during use of the forceps. For patient safety reasons, it is required that portions of the forceps tips that contact the body tissue be constructed or formed of a biocompatible material that will not react with the body tissue.

In the use of prior art forceps, one of the electrical conductors connected to the forceps proximal end is connected to a source of electric power, and the other electrical conductor connected to the forceps proximal end is connected to a ground. The pair of forceps arms function as electrodes. When the forceps arms are manually squeezed by the surgeon to grasp body tissue between the distal end tips of the arms, an electric circuit is completed from one forceps arm tip through the body tissue to the other forceps arm tip. Current passing through the forceps tips and the body tissue heats the forceps tips and the body tissue held between the tips and causes the tissue to be joined or coagulated.

However, the heat produced in the forceps tips can also result in pieces of the body tissue sticking to the tips. During a surgical procedure using bipolar electrosurgical forceps, pieces of body tissue can accumulate on the forceps tips. To prevent or reduce the sticking of body tissue to the forceps tips and accumulating on the forceps tips during a surgical procedure, bipolar electrosurgical forceps have been developed that deliver an irrigating liquid to the forceps tips where the liquid functions as a barrier to tissue sticking to the forceps tips.

The prior art bipolar forceps that include an irrigating feature have employed a single tube that is attached to one of the forceps arms with a distal end of the tube positioned adjacent the distal end tip of the arm. To supply sufficient irrigating liquid to he effective, the single tube was constructed with a 0.065 inch outside diameter and a 0.20 inside diameter. However, the size of the tube circular distal end was found to obstruct the surgeon's vision of the forceps arm distal end. Additionally, the size of the tube circular distal end would interfere with the surgeon squeezing the forceps arm distal end tips together. The circular tube end would prevent the tips from touching when the forceps arms were squeezed and would force the tips apart, resisting the force of the surgeon attempting to close the tips. The circular distal end of the tubing not only created an obstruction to observation of the forceps arm tip and an obstruction to closing the forceps arm tips, the circular shape of the tube distal end tip did not promote wetting of the tip.

Additionally, the prior art forceps often used heat shrink or shrink wrap to attach the irrigation tube to the forceps arm. The heat shrink or shrink wrap was wrapped around the tube and the forceps arm. However, the wrap around the tube and arm creates a pair of projecting ridges on the outside surface of the forceps arm at the opposite ends of the shrink wrap. The ridges created by the shrink wrap presented the potential problem of the ridges engaging with soft tissue as the forceps are moved to a surgery site and possibly damaging the soft tissue.

Furthermore, in prior art irrigating, bipolar forceps, the irrigation tube and the electrical conductor cords projected outwardly from the forceps arm proximal ends in a direction aligned with the forceps arms. With the forceps arms being oriented generally vertically in use, the projecting tube and cords added weight at the distal ends of the forceps arms. The weight added to the distal ends of the forceps arms detracts from the comfort of the surgeon using the forceps.

BRIEF DESCRIPTION OF THE DRAWINGS

Further features of the invention are set forth in the following detailed description of the preferred embodiment of the invention and in the drawing figures.

DETAILED DESCRIPTION OF THE PREFERRED EMBODIMENT

Figure 1:
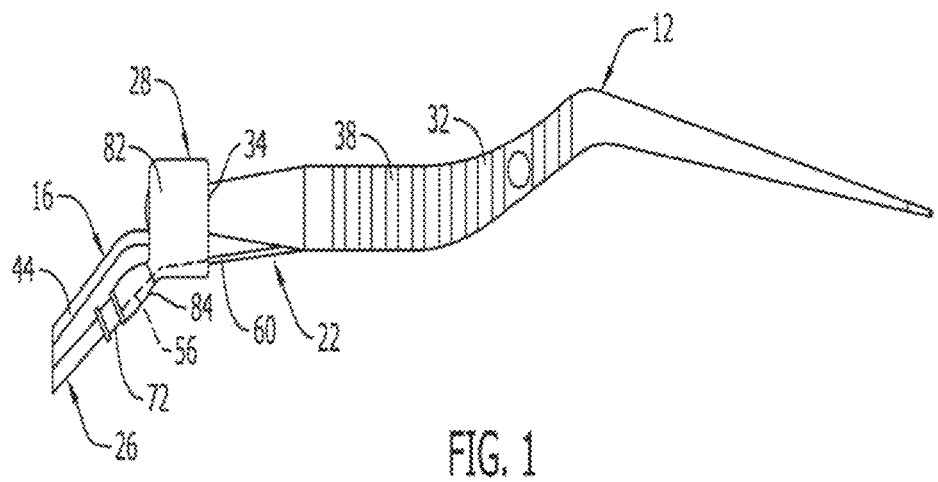
FIG. 1 is a side elevation view of the dual irrigating single use bipolar forceps of the invention.

The present invention provides a disposable or single use, tissue sticking resistant forceps that includes a liquid irrigating feature to each tip of the forceps arms, By being disposable or single use, what is meant is that the forceps are specifically designed for one use in an electrosurgical procedure and for disposal after the one use.

The forceps are comprised of first and second elongate forceps arms. The arms have the same configurations and are laser cut from a blank of aluminum and machined to their final configurations. Stamping, water jet cutting, EDM, plasma cutting, or molding processes could also be used to form the forceps arms.

Electrical conductors are secured to the proximal ends of the pair of arms.

A layer of biocompatible metal, for example silver, is applied to the distal end tips of the pair of arms. To reduce manufacturing costs, the layer of metal has a thickness that is not more than 0.010 of an inch, and is preferably in a range of 0.002 to 0.005 of an inch. This significantly reduces the amount of the expensive biocompatible metal used in the construction of the single use forceps.

A pair of irrigating liquid tubes are secured to the opposed interior surfaces of the forceps arms. The tubes are constructed of non-electrically conductive plastic and are secured to the forceps arms by an adhesive, thereby reducing the costs of securing the tubes to the forceps arms. The distal ends of the tubes are positioned adjacent the distal end tips of the arms and are formed as flat nozzles on the interior surfaces of the arms. The flat nozzle configuration disperses the irrigating liquid across the opposed surfaces of the arm distal end tips and thereby enhances the non-sticking function of the irrigation liquid. The proximal ends of the tubes are positioned adjacent the proximal ends of the forceps arms and are connected in fluid communication with a single supply tube. The single fluid supply tube extends from the proximal ends of the forceps arms to a connector at the opposite end of the supply tube that is adapted to connect the supply tube to a single irrigation fluid source.

The proximal ends of the forceps arms, the connection of the electrical conductors to the proximal ends of the forceps arms and the connection of the irrigation tube proximal ends to the supply tube are all encapsulated in and surrounded by a potting material that forms a base around the forceps arm proximal ends. The base has a primary portion with an exterior surface that extends around the forceps arm proximal ends and around the connection of the electrical conductors to the forceps arms. The base also has a secondary portion having an exterior surface that projects at an angle from the primary portion exterior surface. The secondary portion exterior surface extends around the connection of the supply tube to the irrigation tube proximal ends. The angled orientation of the secondary portion of the base relative to the primary portion of the base directs the supply tube at an angle away from the lengths of the forceps arms and thereby reduces the influence of the weight of the supply tube on the weight at the distal ends of the forceps arms when the forceps are used in a vertical orientation. This in turn reduces the interference of the supply tube with the movement of the forceps arms by a surgeon's hand.

Constructing the forceps in the manner discussed above reduces their manufacturing costs enabling the forceps to be single use, disposable forceps. The forceps also have the advantages of supplying irrigating liquid to the opposed surfaces of both the forceps arm distal end tips without obstructing the surgeon's view of the distal end tips and without interfering with the surgeon squeezing together the distal end tips.

Figure 2:
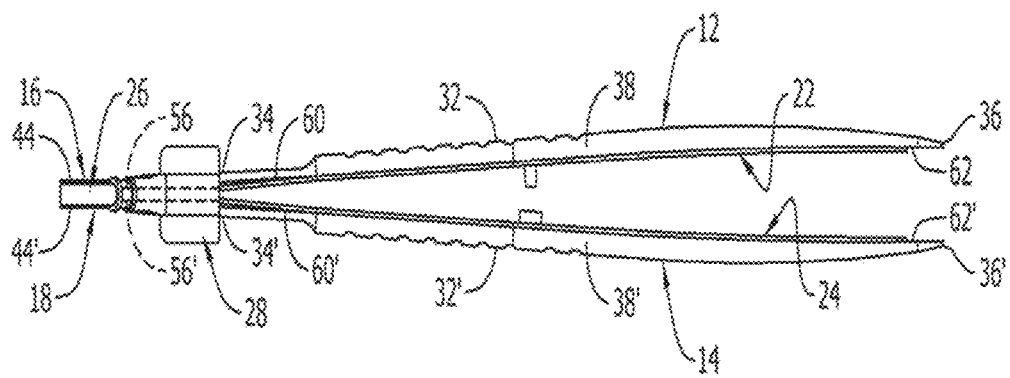
FIG. 2 is a bottom plan view of the forceps of FIG. 1.

FIGS. 1 and 2 show respective side and bottom views of the single use, dual irrigating bipolar forceps of the present invention.

Figure 3:
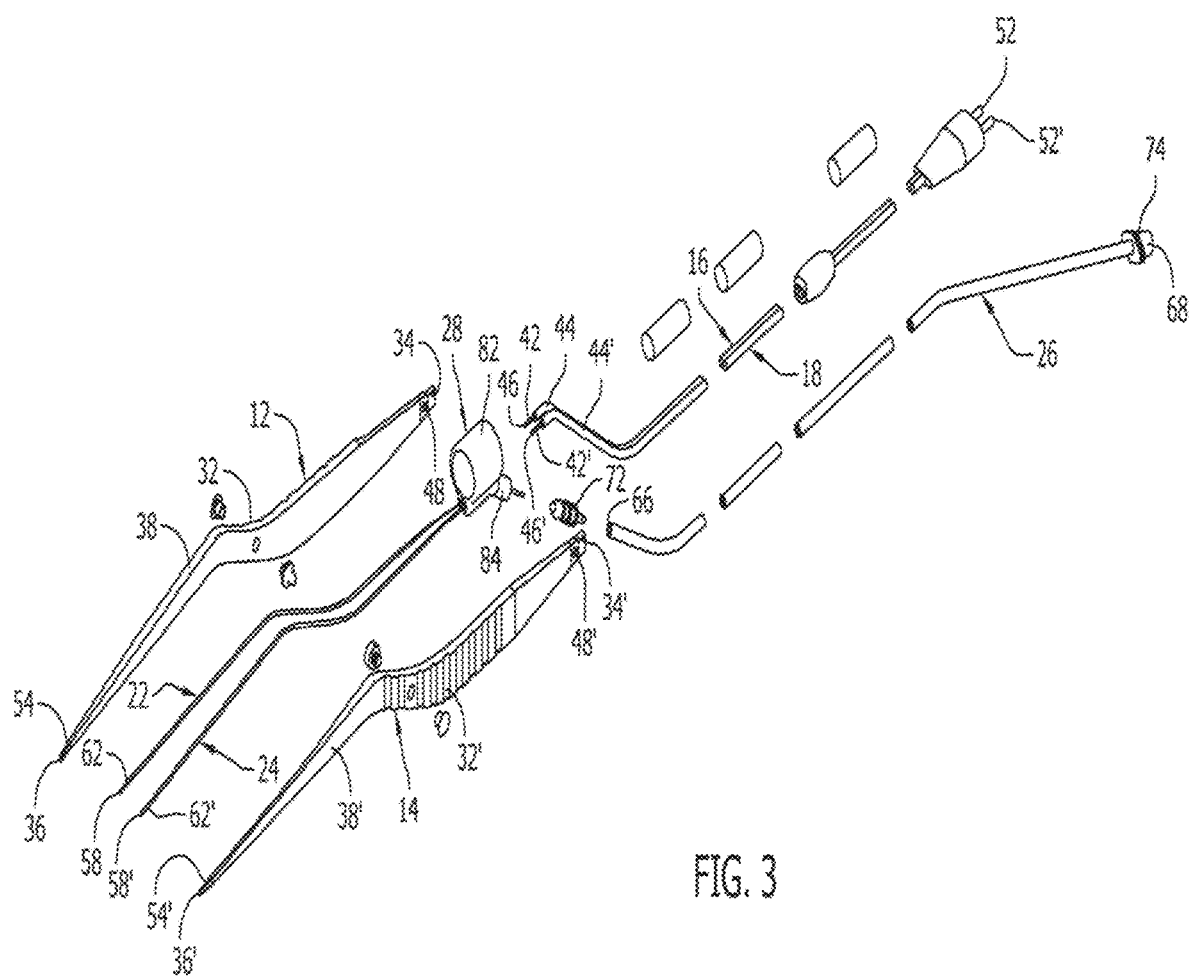
FIG. 3 is a perspective disassembled view of the forceps of FIG. 1.

FIG. 3 is a disassembled view of an embodiment of the forceps. The forceps are specifically designed to be disposable or single use, bipolar electrosurgical forceps with an irrigating feature that reduces or eliminates tissue sticking. The forceps are basically comprised of a pair of forceps arms or electrodes 12, 14, a pair of electrically conductive cords 16, 18, a pair of fluid irrigation tubes 22, 24, an irrigation supply tube 26 and a base 28 As explained below, the construction of the forceps is simplified and comprises a minimum number of parts to reduce the manufacturing costs of the forceps and to make the disposal of the forceps after a single use economically feasible. Furthermore, as explained below, the forceps are constructed with an irrigation feature that provides irrigating liquid to the distal end tips of the forceps arms to reduce or eliminate tissue sticking while avoiding the drawback of prior art forceps having irrigating features The first 12 and second 14 forceps arms are constructed as mirror images of each other. in view of this, the construction of only the first arm 12 is described in detail. The same reference numbers are employed to label the component parts of both forceps arms 12, 14, with the reference numbers of the second forceps arm 14 being followed by a prime ('). The first forceps arm 12 is constructed with a narrow, elongate length having an intermediate portion 32 and opposite proximal 34 and distal 36 ends. The arm intermediate portion 32 is shaped and dimensioned to be held comfortably by a single hand of the surgeon using the forceps. The entire length of the first arm 12 is constructed from a blank of 6061-T6 aluminum that is laser cut to the configuration of the arm shown. In alternate embodiments of the forceps, the arms 12, 14 may be constructed entirely of stainless steel, entirely of brass, entirely of tin, entirely of copper, or entirely of an alloy of these materials, The arms 12, 14 could also be constructed of a plastic material. However, a plastic embodiment of the arms would require an electrical conductor extending the length of the arms in order to enable the arms to function as electrodes of the electrosurgical instrument.

An insulating coating 38 completely covers the intermediate portion 32 of the arm 12. The coating 38 is electrically insulated and may also be thermally insulated. The coating 38 covers only the intermediate portion 32 of the arm 12, leaving the arm proximal end 34 and distal end 36 projecting and exposed from the coating layer 38. A much thinner layer of the insulating coating 38 is applied to the arm 12 of the disposable forceps than would be applied to forceps aims of a reusable forceps. Because the forceps are intended to be disposable or only single use, a thinner layer of the insulating coating 38 may be used without concern for the layer wearing through after repeated uses and sterilizations of the forceps. Applying the thinner layer of insulating coating 38 to the arm 12 reduces the production costs, improves visual and sight access, and reduces the barrier for heat rejection to the environment imposed by a thicker insulating coating. The primary purpose of the insulating coating 38 is to provide electrical insulation for the patient to prevent stray currents from damaging healthy tissue.

The first 16 and second 18 bipolar electrically conducting cords with flexible elongate lengths are connected to the proximal ends 34, 34' of the first 12 and second 14 forceps arms. The two cords 16, 18 are identical in construction, Therefore, the construction of only the first cord 16 is described in detail. The same reference numbers employed in the description of the first cord 16 are also used in labeling the component parts of the second cord 18, but the reference numbers labeling the parts of the second cord 18 are followed by a prime ('). The construction of the cord 16 is for the most part conventional. The cord contains an electrically conductive wire 42 that is covered by an insulated layer 44. A first end 46 of the wire 42 extends from the insulator layer 44 and is electrically connected to the aim proximal end 34. Referring to FIG. 3, the wire first end 46 is inserted through a hole 48 in the arm proximal end 34 and crimped, thereby securing the first cord 16 both mechanically and electrically to the first arm 12. The cord 16 has a flexible, elongate length that extends from the first arm 12 to an electrical connector 52 at the opposite second end of the cord 16. The lengths of the cords 16, 18 allow the forceps arms, 12, 14 to be easily manipulated by the hand of a surgeon when the electrical connectors 52, 52' are connected to a source of electric power. High strand count wire is used in the cord 16 for maximum flexibility. By crimping the wire 16 onto the arm proximal end 34, the costs of a removable plug on the cord is eliminated, and also manufacturing difficulties associated in attaching a traditional connecting pin to the arm 12 are overcome.

Providing integral electrical conducting cords on the forceps eliminates the costs of the electrical male plugs on the forceps and the removable conductor cords with female plug receptors of prior art bipolar forceps. This reduces manufacturing costs of the forceps of the invention compared to that of prior art bipolar forceps.

The distal ends 36, 36' of the first 12 and second 14 forceps arms are covered with stick resistant tip layers 54, 54', on at least the opposing surfaces of the tips. The tip layer 54 in one embodiment of the invention is a thin layer of biocompatible material applied to the distal ends 36, 36' of the forceps arms 12, 14. The thickness of the biocompatible material on the arm distal end 36 is kept to a minimum to reduce costs, and is not more than 0.010 of an inch. More preferably, the thickness of the layer of biocompatible material on each arm tip is not more than 0.005 of an inch or is in a range of 0.002 of an inch to 0.005 of an inch. The biocompatible material is preferably pure silver or gold. The thickness of 0.002 to 0.005 of an inch for the layer of biocompatible material is a specification for the silver plating process. Smaller thicknesses are also acceptable. The thickness range of 0.002. to 0.005 of an inch is chosen to be slightly more conservative in order to allow for some minor material removal when the tip layers are polished prior to packaging. A final layer thickness of 0.001 to 0.003 is most preferred. A silver plating thicknesses less than 0.001 and even less than 0.0005 of an inch is suitable in some embodiments.

The minimal thickness of the biocompatible metal on the distal ends 36, 36' of the forceps arms reduces the costs of materials used in the construction of the forceps with tissue cauterizing tips, reduces the costs of manufacturing the forceps, and thereby enables the forceps to be disposable or single use forceps.

The first 22 and second 24 fluid irrigation tubes are secured to the opposed, interior surfaces of the respective first 16 and second 18 forceps arms on the insulation 38, 38' coating the arms. The irrigation tubes 22, 24 have basically the same constructions. In view of this, the construction of only one of the irrigation tubes 22 is described in detail. The same reference numbers are employed to label the component parts of both of the irrigation tubes 22, 24, with the reference numbers of the second irrigation tube 24 being followed by a prime ('). The first irrigation tube 22 has a flexible length with opposite proximal 56 and distal 58 ends. The entirety of the tube length is constructed of a transparent, biocompatible, non-electrically conductive plastic material, for example polycarbonate capillary tubing. Employing non-conductive plastic tubing avoids any short circuiting of the arm distal end tips 36, 36'. In the operative embodiment of the forceps, the tube 22 has a 500 micron or 0.020 inch outer diameter dimension and a 250 micron or 0.010 inch interior diameter dimension. This small tube size on the forceps is less obstructive visually and functionally. However, because two tubes 22, 24 are employed on the forceps there is still a sufficient flow of irrigation fluid supplied to arm tips 36, 36'. The tube distal end 58 is secured by an adhesive to the insulation 38 coating the interior surface of the first arm 12 immediately adjacent or juxtaposed with the tip layer 54 of the arm. From the tube distal end 58 a majority of the length of the tube is also secured to the interior surface of the forceps aim 12 by the adhesive. As can be seen in FIG. 1, a portion 60 of the length of the first, tube 22 adjacent the tube proximal end 56 is not secured to the first forceps arm 12. The use of a plastic tube and an adhesive securing the first tube 22 to the first forceps arm 12 reduces the manufacturing costs of the forceps.

Because the forceps are disposable, it is not necessary that the tube be secured to the arm in a manner that will stand up to repeated sterilizations. Additionally, employing the adhesive to secure the first tube 22 to the interior surface of the first forceps arm 12 maintains a smooth exterior surface of the first forceps arm 12 and avoids any projections or ridges on the exterior surface that could potentially damage body tissue in use of the forceps.

Figure 4:
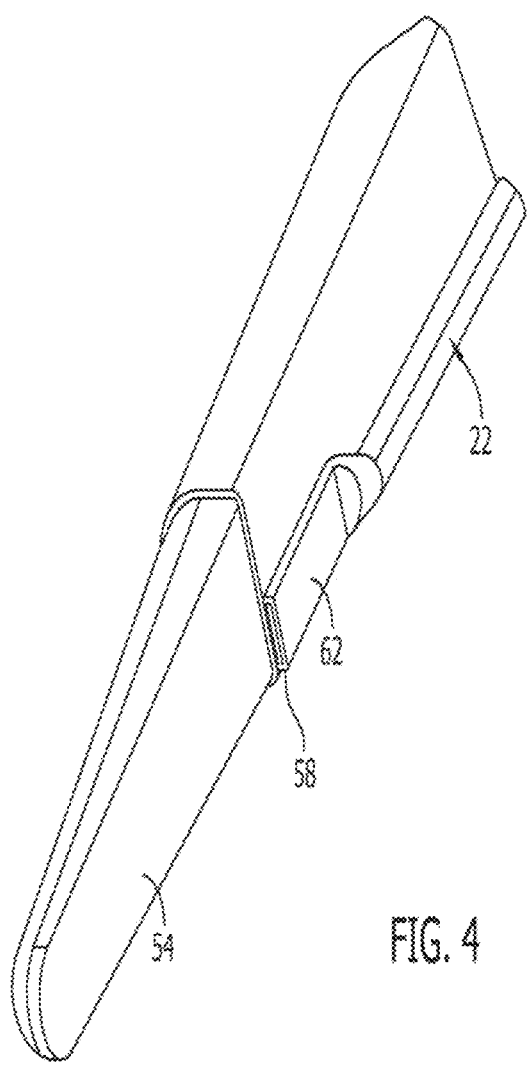
FIG. 4 is an enlarged partial view of the distal end tip of one of the forceps arms.

The majority of the length of the first tube 22 from the tube proximal end 56 toward the tube distal end 58 has a circular cross-section. However, as seen in FIG. 4, a portion of the first tube 22 at the tube distal end 58 is effectively flattened, forming an elongated nozzle shape 62 having an oblong cross-section at the distal end 58 of the tube 22. The nozzle shape 62 has a length of approximately 2.5 mm. The elongated shape of the nozzle 62 and its position adjacent the tip layer 54 of the first arm 12 promotes wetting of the interior surface of the first arm tip layer 54. The elongated configuration of the nozzle 62 disburses the irrigating liquid across the arm distal end tip 36 and thereby enhances the non-sticking function of the irrigation liquid. The elongated nozzle 62 also avoids drop formation in the irrigating liquid dispensed from the nozzle. Additionally, the flattened and elongated shape of the nozzle 62 does not interfere with the surgeon squeezing together the forceps arms 12, 14 to grip tissue between the distal ends of the arms, as occurred in prior art forceps.

The proximal ends 56, 56' of both tubes 22, 24 extend from the portions of the tubes adhered to the interior surfaces of the arms 12, 14 to positions adjacent the proximal ends 34, 34' of the arms. Here the tube proximal ends 56, 56' are connected in fluid communication with the single supply tube 26.

The supply tube 26 has a flexible length between opposite first 66 and second 68 ends of the tube. In the illustrated embodiment the supply tube 24 is constructed from transparent polyurethane tubing having a 1/16 inch inner diameter dimension and a 1/8 inch outer diameter dimension. A transparent polycarbonate barbed tube fitting 72 is provided at the supply tube first end 66. The fitting 72 connects the supply tube first end 66 with the proximal ends 56, 56' of the respective first 22 and second 24 irrigation tubes. The opposite second end 68 of the supply tube is provided with a gamma stabilized polypropylene luer fitting 74. The luer fitting 74 is adapted to connect the supply tube 24 to a single irrigation liquid source.

The forceps arm proximal ends 34, 34', the connection of the cord first ends 46, 46' to the forceps arm proximal ends 34, 34', and the connection of the irrigation tube proximal ends 56, 56' to the fitting 72 at the supply tube first end 66 are all encapsulated in and surrounded by a potting material that forms the base 28 around the forceps arm proximal ends 34, 34'. The base 28 has a primary portion with a generally cylindrical exterior surface 82 that extends around the forceps arm proximal ends 34, 34' and around the cord first ends 46, 46'. The base 28 also has a secondary portion having a generally cylindrical exterior surface 84 that projects at an angle from the primary portion exterior surface 82. The secondary portion exterior surface 84 extends around the connection of the irrigation tube proximal ends 56, 56' with the first end fitting 72 of the supply tube 26. The angled orientation of the secondary portion 84 of the base relative to the primary portion 82 of the base directs the liquid supply tube 26 at an angle away from the lengths of forceps arms 12, 14, thereby reducing the influence of the weight of the supply tube 26 containing irrigation liquid on the weight at the distal ends 36, 36' of the forceps arms when the forceps are being used in a vertical orientation. This in turn reduces the interference of the liquid supply tube 26 with the movement of the forceps arms 12, 14 by a surgeon's hand.

Constructing the forceps in the manner discussed above reduces the manufacturing costs of the forceps, thereby enabling the forceps to be single use, disposable forceps. The construction of the forceps described above also provides the advantage of supplying irrigating liquid to the opposed surfaces of both the forceps arm distal end tips 36, 36' without obstructing the surgeon's view of the of the distal end tips and without interfering with the surgeon squeezing together the distal end tips.

As various modifications could be made in the construction of the apparatus herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above described exemplary embodiments, but should be defined only in accordance with the following claims appended hereto and their equivalents.

The invention claimed is:

1. A forceps comprising:
   first and second arms, each of the first and second arms having an elongate length with opposite proximal and distal ends and having opposite inner and outer surfaces that extend the elongate length of each of the first and second arms, the proximal ends of the first and second arms being connected together with the inner surfaces of the first and second arms opposing each other, and the distal ends of the first and second arms being constructed as tissue cauterizing tips; and
   a first irrigation tube having a length with opposite proximal and distal ends, at least a part of the first irrigation tube length being secured to the first arm with the first irrigation tube length extending from the first irrigation tube proximal end adjacent the first arm proximal end, across the elongate length of the first arm to the first irrigation tube distal end adjacent the first arm distal end, the first irrigation tube having a cross-section configuration along its length, wherein the cross-section configuration is a substantially circular configuration as the first irrigation tube extends from the first irrigation tube proximal end toward the first irrigation tube distal end and wherein the cross-section configuration changes from the substantially circular configuration to an oblong configuration at a portion of the first irrigation tube length adjacent the first irrigation tube distal end with the cross-section configuration of the first irrigation tube distal end being oblong.

2. The forceps of claim 1, further comprising a second irrigation tube having a length with opposite proximal and distal ends, with at least a part of the second irrigation tube being secured to the second arm with the second irrigation tube length extending from the second irrigation tube proximal end adjacent the second arm proximal end, across the elongate length of the second arm to the second irrigation tube distal end adjacent the second arm distal end.

3. The forceps of claim 2, wherein a cross-section configuration of the second irrigation tube is a substantially circular configuration as the second irrigation tube extends from the second irrigation tube proximal end toward the second irrigation tube distal end and wherein the cross-section configuration of the second irrigation tube changes from the substantially circular configuration to an oblong configuration at a portion of the second irrigation tube length adjacent the second irrigation tube distal end with the cross-section configuration of the second irrigation tube distal end being oblong.

4. The forceps of claim 2, further comprising:
   an irrigation fluid supply tube having a length with opposite first and second ends, the irrigation fluid supply tube first end being connected and in communication with both of the first and second irrigation tube proximal ends and the irrigation fluid supply tube second end being connectable to a source of irrigation fluid.

5. The forceps of claim 4, further comprising:
   a base enclosing the first and second arm proximal ends and enclosing a connection of the irrigation fluid supply tube first end to both of the first and second irrigation tube proximal ends.

6. The forceps of claim 5, wherein the base has a primary portion with an exterior surface that extends around the proximal ends of the first and second arms and the base has a secondary portion having an exterior surface that projects at an angle from the primary portion exterior surface and extends around the irrigation fluid supply tube adjacent the connection of the irrigation fluid supply tube first end to the first and second irrigation tube proximal ends.

7. The forceps of claim 1, wherein at least a part of the first irrigation tube length is secured to the first arm by an adhesive.

8. The forceps of claim 7, wherein the first irrigation tube is secured by the adhesive to the inner surface of the first arm.

9. The forceps of claim 1, wherein the first irrigation tube extends across only the inner surface of the first arm.

10. The forceps of claim 1, further comprising first and second electrical conductors, each electrical conductor having a flexible elongate length, the first electrical conductor being electrically connected to the first arm and the second electrical conductor being electrically connected to the second arm.

11. The forceps of claim 2, wherein the first and second irrigation tubes are plastic tubes.

12. The forceps of claim 2, wherein the first and second irrigation tubes are constructed of an electrically insulating material.

13. A forceps comprising:
   first and second arms, each of the first and second arms having an elongate length with opposite proximal and distal ends and having opposite inner and outer surfaces that extend the elongate length of each of the first and second arms, the proximal ends of the first and second arms being connected together with the inner surfaces of the first and second arms opposing each other, and the distal ends of the first and second arms being constructed as tissue cauterizing tips; and
   first and second plastic irrigation tubes, each of the first and second plastic irrigation tubes having a length with opposite proximal and distal ends, at least a part of the first plastic irrigation tube length being secured to the first arm with the first plastic irrigation tube length extending from the first plastic irrigation tube proximal end adjacent the first arm proximal end, across the elongate length of the first arm to the first plastic irrigation tube distal end adjacent the first arm distal end, the first plastic irrigation tube having a cross-section configuration along its length, wherein the cross-section configuration of the first plastic irrigation tube is a substantially circular configuration as the first plastic irrigation tube extends from the first plastic irrigation tube proximal end toward the first plastic irrigation tube distal end and wherein the cross-section configuration of the first plastic irrigation tube changes from the substantially circular configuration to an oblong configuration at a portion of the first plastic irrigation tube length adjacent the first plastic irrigation tube distal end with the cross-section configuration of the first plastic irrigation tube distal end being oblong, and at least a part of the second plastic irrigation tube length being secured to the second arm with the second plastic irrigation tube length extending from the second plastic irrigation tube proximal end adjacent the second arm proximal end, across the elongate length of the second arm to the second plastic irrigation tube distal end adjacent the second arm distal end.

14. The forceps of claim 13, wherein the second plastic irrigation tube has a cross-section configuration along its length, wherein the cross-section configuration of the second plastic irrigation tube is a substantially circular configuration as the second plastic irrigation tube extends from the second plastic irrigation tube proximal end toward the second plastic irrigation tube distal end and wherein the cross-section configuration of the second plastic irrigation tube changes from the substantially circular configuration to an oblong configuration at a portion of the second plastic irrigation tube length adjacent the second plastic irrigation tube distal end with the cross-section configuration of the second plastic irrigation tube distal end being oblong.

15. The forceps of claim 14, further comprising:
an irrigation fluid supply tube having a length with opposite first and second ends, the irrigation fluid supply tube second end being connectable to a source of irrigation fluid and the irrigation fluid supply tube first end being connected and in communication with both of the first and second plastic irrigation tube proximal ends.

16. The forceps of claim 15, further comprising:
a base enclosing the first and second arm proximal ends and a connection of the irrigation fluid supply tube first end to both of the first and second plastic irrigation tube proximal ends.

17. The forceps of claim 16, wherein the base has a primary portion with an exterior surface that extends around the proximal ends of the first and second arms and the base has a secondary portion with an exterior surface that projects at an angle from the primary portion exterior surface and extends around the connection of the irrigation fluid supply tube first end to the first and second plastic irrigation tube proximal ends.

18. The forceps of claim 13, wherein the first and second plastic irrigation tubes are secured to the inner surfaces of the respective first and second arms.

19. The forceps of claim 13, wherein the first and second plastic irrigation tubes extend across only the inner surfaces of the respective first and second arms.

20. The forceps of claim 13, further comprising:
first and second electrical conductors, each electrical conductor having a flexible elongate length, the first electrical conductor being electrically connected to the first arm and the second electrical conductor being electrically connected to the second arm.

* * * * *